(12) United States Patent
Lee et al.

(10) Patent No.: US 6,288,841 B1
(45) Date of Patent: Sep. 11, 2001

(54) OPTICAL MECHANISM FOR PRECISELY CONTROLLING THE ANGLE OF AN INCIDENT LIGHT BEAM WITHIN A LARGE INCIDENT ANGLE RANGE

(75) Inventors: Solomon J. H. Lee; Chih-Kung Lee; Tony C. H. Lin; Shih-Jui Chen; Shu-Sheng Lee, all of Taipei; Shuen-Chen Shiue, Keelung, all of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/475,001

(22) Filed: Dec. 30, 1999

(51) Int. Cl.[7] .................................................. G02B 27/10
(52) U.S. Cl. ........................ 359/618; 359/626; 359/853; 356/328
(58) Field of Search ..................................... 359/618, 619, 359/621, 626, 853; 250/226; 356/328, 369

(56) References Cited

U.S. PATENT DOCUMENTS 5,900,981 * 5/1999 Oren et al. ........................... 359/619
5,903,386 * 5/1999 Mantravadi et al. ................. 359/853
5,969,872 * 10/1999 Oren et al. ............................ 359/621
6,122,107 * 9/2000 Koch et al. ........................... 359/618

* cited by examiner

Primary Examiner—Loha Ben
(74) Attorney, Agent, or Firm—Jiawei Huang; J. C. Patents (57) ABSTRACT

An optical path overlapping type incident angle changeable optical mechanism according to the invention allows an incident light beam to be incident onto a measured range of a sample within a large incident angle range. The optical mechanism includes a reflecting prism reflecting the incident light beam to generate a reflected light beam having an angle of 90° with respect to the incident light beam; a concave parabolic cylindric mirror guiding the reflected light beam coming from the reflecting prism to a measured range of a detect-waiting sample to thereby be further reflected to generate a detect-waiting light beam; a concave cylindric mirror used to make the detect-waiting light beam incident onto/reflected by the reflecting prism so as to overlap with the incident light beam; and a light beam splitting means used to separate the detect-waiting light beam from the incident light beam.

36 Claims, 10 Drawing Sheets

OPTICAL MECHANISM FOR PRECISELY CONTROLLING THE ANGLE OF AN INCIDENT LIGHT BEAM WITHIN A LARGE INCIDENT ANGLE RANGE

BACKGROUND OF THE INVENTION

1. Field of the Invention

The invention relates to an optical mechanism, and in particular to an optical mechanism for precisely controlling the angle of an incident light beam within a large incident angle range.

2. Description of the Related Art

Currently, an optical measuring apparatus usually needs an optical mechanism system that can specify a single detecting point under any circumstances when measuring a specific position. For example, to prevent design troubles for an ellipsometer during the above-stated measurement, one method is that an incident angle is fixed to perform a multi-wave length measurement, and then the number of unknown quantities is decreased with the cooperation of an appropriate material model. However, this method completely depends on the accuracy of the dispersion formula of the material model, and therefore, it is theoretically inferior to changing the incident angle. It is noted that the principle of changing an incident angle is to measure the intensity or the phase of a reflected light beam by precisely controlling an incident angle or largely changing the incident angle. Then, a signal corresponding to a specific position can be obtained using an inverse mathematical calculation. Nevertheless, it is necessary to have a particular design on the optical mechanism system with a measured point fixed because the angle of the incident light beam is continuously changed.

Figure 1:
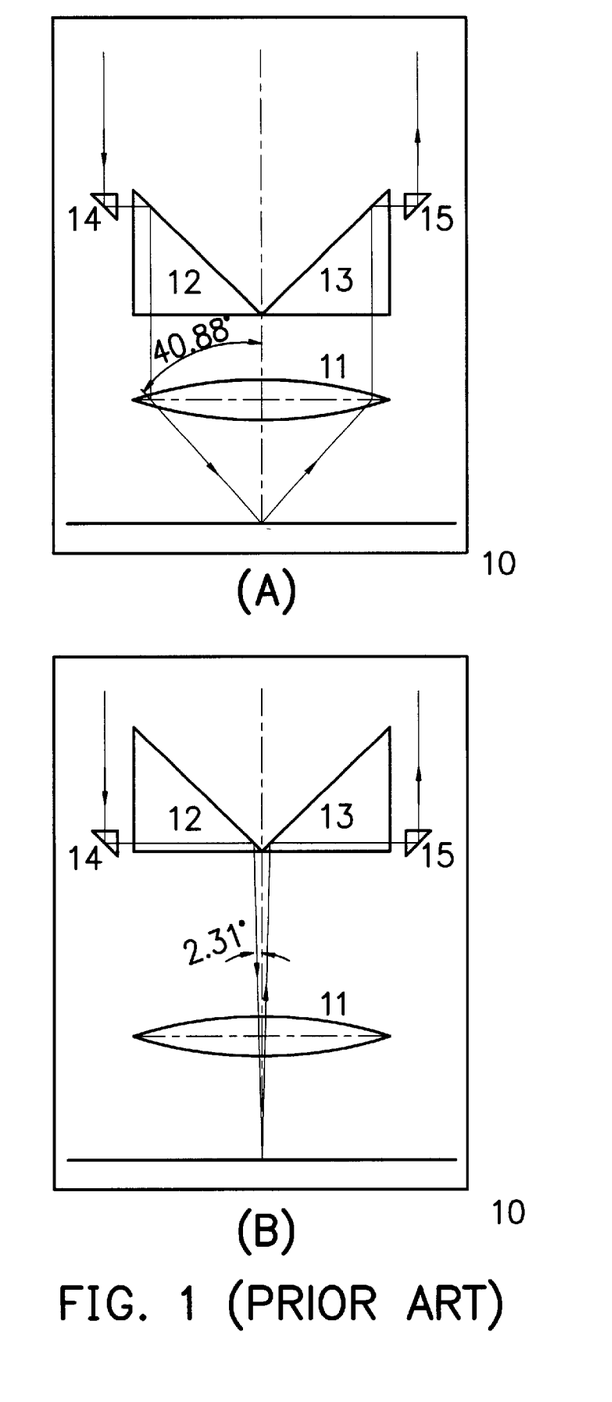
FIGS. 1(A) and 1(B) are schematic views showing a conventional single lens focusing type optical mechanism.
Figure 2:
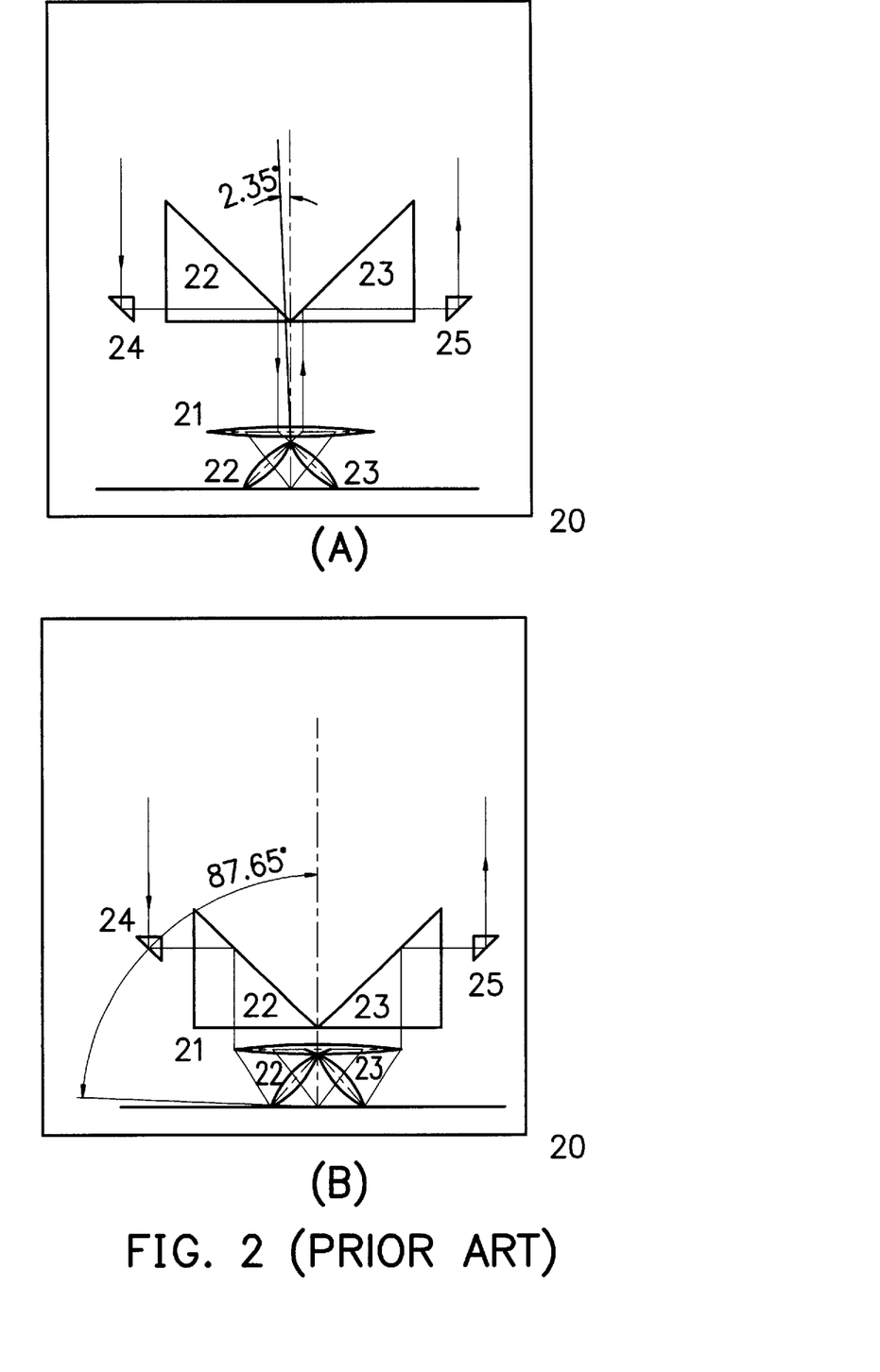
FIGS. 2(A) and 2(B) are schematic views showing a conventional multi-lens focusing type optical mechanism.

Basically, the conventional incident angle changeable optical mechanism can be grouped into an arm-rotating type, a single lens focusing type 10 (referring to FIGS. 1(A) and 1(B)) and a multi-lens focusing type 20 (referring to FIGS. 2(A) and 2(B)) of optical mechanisms. However, these optical mechanisms have several defects, for example, the change of an incident angle is too small, and the spherical phase difference can not be compensated, resulting in more complicated optical mechanisms. Therefore, it is very difficult to find an optical mechanism which can precisely provide a large range of incident angle and make optical paths more closed.

As to the arm-rotating type optical mechanism, measuring a changeable incident angle is performed by using two rotating motors to drive two rotating arms called an incident arm and a reflecting arm, wherein a transmitting terminal is set on the incident arm while a receiving terminal is set on the reflecting arm. However, the optical head of this arm-rotating type optical mechanism must be divided into two parts on function and space because of the existence of the two rotating motors. This will cause a large volume. Meanwhile, it is difficult to increase the accuracy of this optical mechanism, resulting in an expensive cost.

With respect to the single lens focusing type incident angle changeable optical mechanism 10 as shown in FIGS. 1(A) and 1(B), it includes a lens 11, two fixed reflecting prisms 12, 13 and two moveable reflecting prisms 14, 15 which can be moved up and down by use of a single axis shift stage. When the reflecting prisms 14, 15 are moved to the top level of the reflecting prisms 12, 13, a corresponding incident angle is approximately 2°. As shown in FIG. 1(A), when the reflecting prisms 14, 15 is moved to the bottom level of the reflecting prisms 12, 13, a corresponding incident angle is approximately 41°. Since it is difficult to have the numerical aperture (NA) of a single lens more than 1, an incident angle can be hardly over 45°. This results in that the incident angle is only approximately located in the range of 0–45°. That is, an incident angle over 45° can not be provided. Moreover, the single lens focusing type optical mechanism has a problem of spherical phase difference, so it will cause non-unique focuses.

As to the multi-lens focusing type incident angle changeable optical mechanism developed by modifying the single lens focusing type optical mechanism (as shown in FIGS. 2(A) and 2(B)), it includes lenses 21, 22, 23, two fixed reflecting prisms 22, 23 and two moveable reflecting prisms 24, 25 which can be moved up and down by use of a single axis shift stage. With this multi-lens focusing type incident angle changeable optical mechanism, an incident light beam and a reflected light beam can be still parallel to an original light beam after traveling a specific distance. As shown in FIG. 2(A), when the reflecting prisms 24, 25 is moved to the top level of the reflecting prisms 22, 23, a corresponding incident angle is approximately 2°. As shown in FIG. 2(B), when the reflecting prisms 24, 25 is moved to the bottom level of the reflecting prisms 22, 23, a corresponding incident angle is approximately 88°. The multi-lens focusing type incident angle changeable optical mechanism 20 not only can make optical paths more close to each other, but also can have a larger incident angle. However, it is very difficult for the conventional multi-lens focusing type incident angle changeable optical mechanism on design, assembly and calibration. As stated above, the general focusing lenses having a problem of spherical aberration will cause focuses non-unique. Furthermore, with such conventional incident angle changeable optical mechanisms, a fixed point can not be measured through a transparent or translucent dielectric.

SUMMARY OF THE INVENTION

In view of the above, the invention is to provide a series of incident angle changeable optical mechanisms by which space limitation on optical paths can be greatly improved thereby to achieve miniaturization, and a specific point can be measured through a transparent or translucent dielectric.

An optical path overlapping type incident angle changeable optical mechanism according to the invention allows an incident light beam to be incident onto a measured range of a sample within a large incident angle range. This optical mechanism includes a reflecting prism reflecting the incident light beam to generate a reflected light beam having an angle of 90° with respect to the incident light beam; a concave parabolic cylindric mirror guiding the reflected light beam coming from the reflecting prism to a measured range of a detect-waiting sample to thereby be further reflected to generate a detect-waiting light beam; a concave cylindric mirror used to make the detect-waiting light beam incident onto/reflected by the reflecting prism so as to overlap with the incident light beam; and a light beam splitting means used to separate the detect-waiting light beam from the incident light beam.

A dielectric penetrating/optical path overlapping type incident angle changeable optical mechanism according to the present invention allows an incident light beam to penetrate an observing dielectric having a specific thickness and then incident onto a measured range of a sample within a large incident angle range. This optical mechanism includes a reflecting prism which reflects the incident light beam to generate a reflected light beam having an angle of 90° with respect to the incident light beam; a quasi-concave parabolic cylindric minor used to make the reflected light beam coming from the reflecting prism penetrate the observing dielectric and then incident onto/reflected by a measured range of a detect-waiting sample to thereby generate a detect-waiting light beam; a quasi-concave cylindric mirror used to change the traveling direction of the detect-waiting light beam so as to make the detect-waiting light beam incident onto/reflected by the reflecting prism to thereby overlap with the incident light beam; and a light beam splitting means used to separate the detect-waiting light beam from the incident light beam.

BRIEF DESCRIPTION OF THE DRAWINGS

The invention will be more fully understood from the detailed description given hereinbelow and the accompanying drawings which are given by way of illustration only, and thus do not limit the present invention, and wherein.

DETAILED DESCRIPTION OF THE PREFERRED EMBODIMENTS

Figure 3:
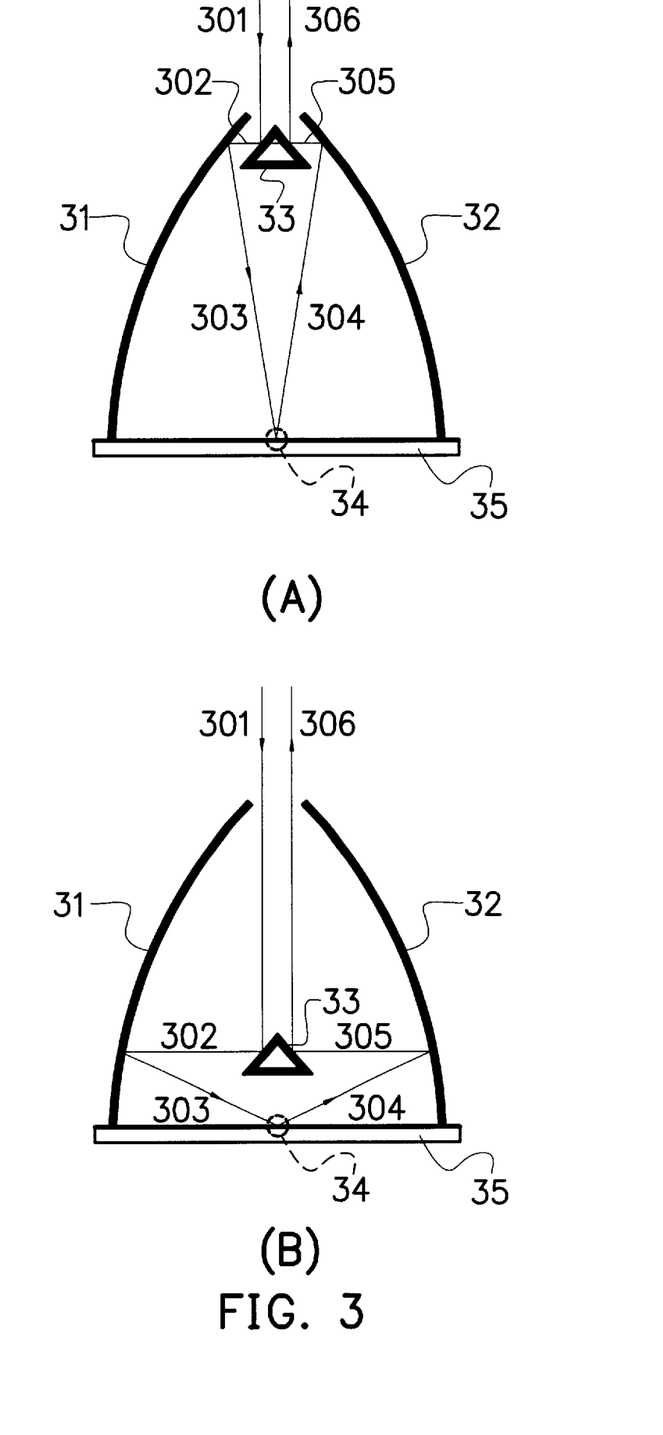
FIGS. 3(A) and 3(B) are schematic views showing an optical path splitting type incident angle changeable optical mechanism according to the present invention.

The present invention can be divided into an optical path splitting type incident angle changeable optical mechanism and an optical path overlapping type incident angle changeable optical mechanism. The optical path splitting type incident angle changeable optical mechanism such as a parabolic mirror type incident angle changeable optical mechanism shown in FIGS. 3(A) and 3(B) includes two parabolic mirrors 31, 32 and a reflecting prism 33 which can be moved up and down by a single axis shift stage. After an incident light beam 301 is reflected by the reflecting prism 33, it is changed into a light beam 302 parallel to the main axis of the parabolic mirrors 31, 32. With this property that the light beam 302 parallel to the main axis, using different incident angles to measure a single specific point can be achieved by moving the reflecting prism 33. In addition, after a reflected light beam 304 is reflected by the parabolic mirror 32 and the reflecting prism 33 in order, it is generated a reflected light beam 306 parallel to the original incident light beam 301, but not overlap with each other. Since the optical paths of the incident light beam 301 and the reflected light beam 306 are separated from each other by means of the reflectinig prism 33, it is very easy for this structure to detect the reflected light beam 306 using an optical detector or an optical microscope. Moreover, the relationship between the intensity and phase of the measured light beam can be obtained, and the property of a test-waiting sample can be calculated according to another measuring structure. Accordingly, the optical path splitting type incident angle changeable optical mechanism can make optical paths close to each other and have a very large range of incident angle. That is, the equivalent numerical aperture is much larger than 1, even approximate to infinity. In addition, the optical path splitting type incident angle changeable optical mechanism has no aberration problem on geometry.

Figure 4:
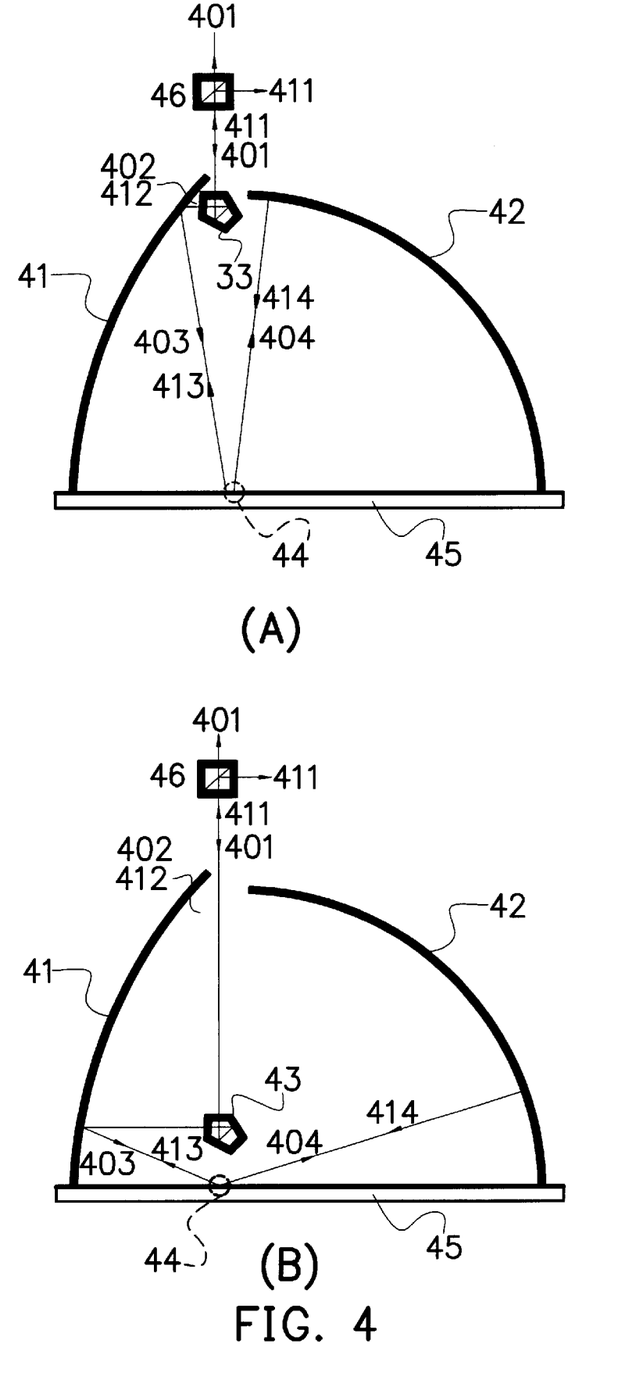
FIGS. 4(A) and 4(B) are schematic views showing an optical path overlapping type incident angle changeable optical mechanism according to the present invention.

As to the optical path overlapping type incident angle changeable optical mechanism such as a parabolic spherical mirror type incident angle changeable optical mechanism shown in FIGS. 4(A) and 4(B), it is constructed by replacing the parabolic mirror of the parabolic mirror type incident angle changeable optical mechanism with a concave spherical mirror. Meanwhile the spherical center is overlapped with a specific measured point, and the optical paths of an incident light beam and a reflected light beam are overlapped by use of a pentagonal reflecting prism. As shown in FIGS. 4(A) and 4(B), the parabolic spherical mirror type incident angle changeable optical mechanism includes a parabolic mirror 41, a concave spherical mirror 42, a pentagonal reflecting prism 43 which can be moved up and down by a single axis shift stage and a non-polarized beam splitter 46. After an incident light beam 401 is reflected by the pentagonal prism 43 and the parabolic mirror 41 in sequence, a light beam 403 formed is incident to/reflected by a fixed point 44 of a detect-waiting sample 45 to thereby generate a reflected light beam 404 which is perpendicularly incident to the concave spherical mirror 42. After further reflected by the concave spherical mirror 42, it becomes a light beam 414 along an original optical path and reflected by the same fixed point 44 to generate a light beam 413. Then, the light beam 413 is further reflected by the parabolic mirror 41 and the pentagonal prism 43 in order to generate a light beam 411. As shown in FIGS. 4(A) and 4(B), the overlapped incident light beam 401 and the reflected light beam 411 are split from each other through a non-polarized beam splitter 46. The property on the surface of the test-waiting sample 45 can be evaluated by the relationship of the intensity and phase of the reflected light beam 411 using an optical detector or an optical microscope.

The pentagonal prism 43 is used to make the light beam 402 leaving therefrom perpendicular to the incident light beam 401 thereby to ensure that the incident light beam 401 is parallel to the parabolic mirror type incident angle changeable optical mechanism. This will not generate an optical axis non-parallel light beam caused by factors, such as assembly and non-accuracy of the calibration of the triangular prism 33 of the parabolic mirror type incident angle changeable optical mechanism.

Figure 5:
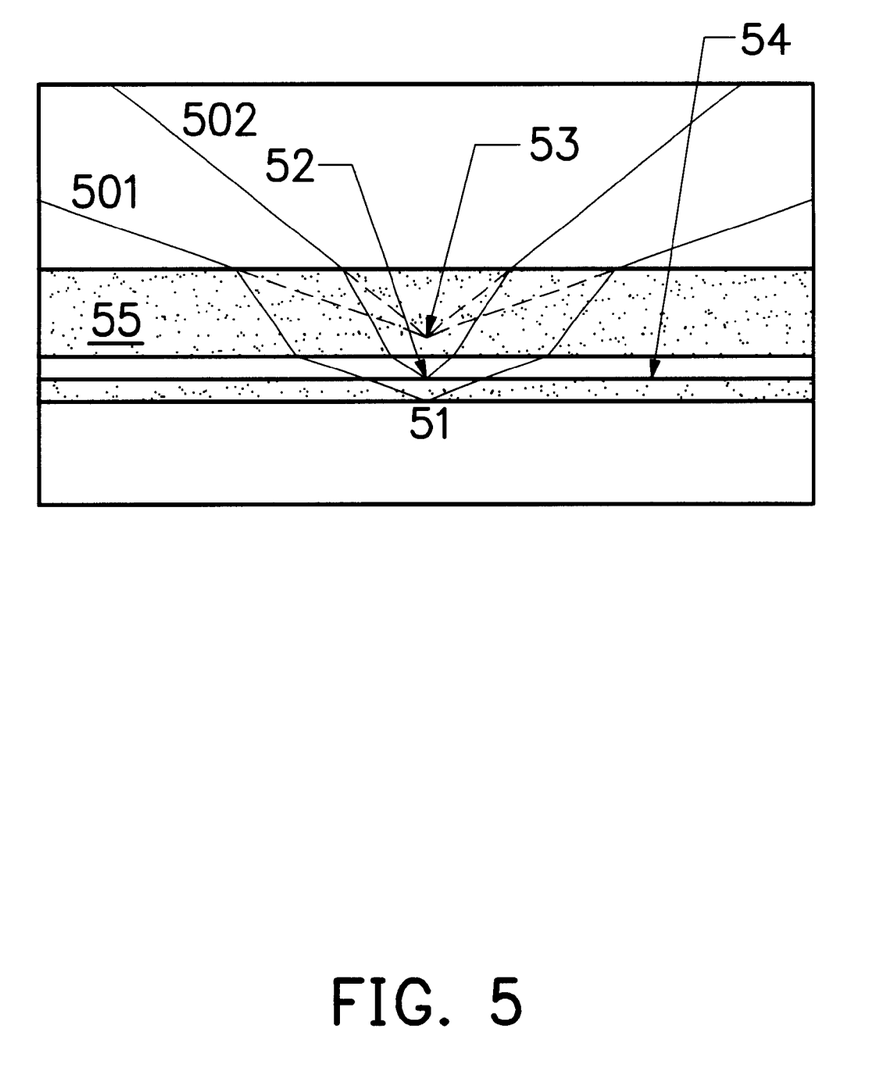
FIG. 5 is a schematic view showing that incident light beams with different incident angles can not be focused on an originally set measured point.

The optical path splitting type and the optical path overlapping type incident angle changeable optical mechanisms are mainly used to directly detect the sample. In order to change the angle of an incident light beam and penetrate a transparent or translucent observing dielectric (such as plastic or glass) over the sample to thereby achieve a specific point detection on the sample, the invention further develops a dielectric penetrating/optical path splitting type incident angle changeable optical mechanism and a dielectric penetrating/optical path overlapping type incident angle changeable optical mechanism where the combination of a quasi-parabolic mirror and quasi-concave spherical mirror is used to detect a fixed detected point of a sample 54 through a transparent or translucent observable dielectric 55. In FIG. 5, incident light beams 501, 502 with different incident angles can not be focused on an originally set measured point 51 because of refraction effect. This will make the detected point shift up and down to be focused on points 52, 53, respectively, resulting in an error on the measurement. To resolve this problem, a quasi-parabolic mirror type optical mechanism with aberration calibration is provided.

Figure 6:
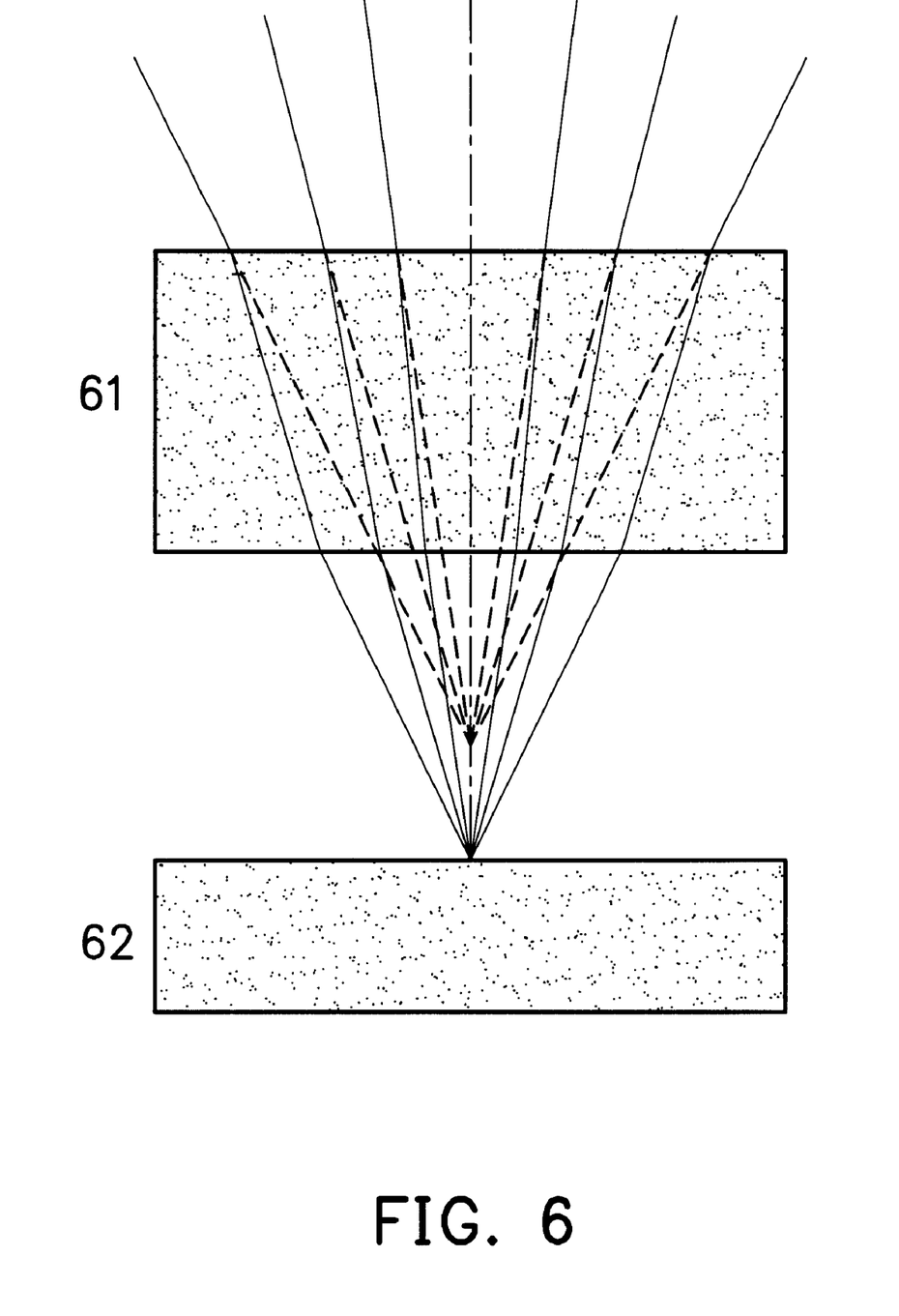
FIG. 6 is a schematic view showing that a single fixed detected point can be obtained by appropriately selecting and designing lenses.

The quasi-parabolic mirror type optical mechanism with aberration calibration uses the focusing function of a lens to provide a capability of changing an incident angle. Since the spherical aberration of a spherical lens is complementary to the detected point shifted by an observing dielectric. Therefore, a single fixed detected point as shown in FIG. 6 can be obtained by appropriately selecting and designing lenses when measuring. The spherical aberration caused by the lens can compensate the deviation of the detected point caused by the observing dielectric 61 to handily make the two defects on optical design compensate with each other, but the practical leans design is difficult to attain this purpose. With this reason, reflecting mirrors are used to change the incident angle. Meanwhile, with the design of the quasi-parabolic mirror and the quasi-concave spherical mirror, it can measure a single detected point through an observing dielectric, using various incident angles.

Figure 7:
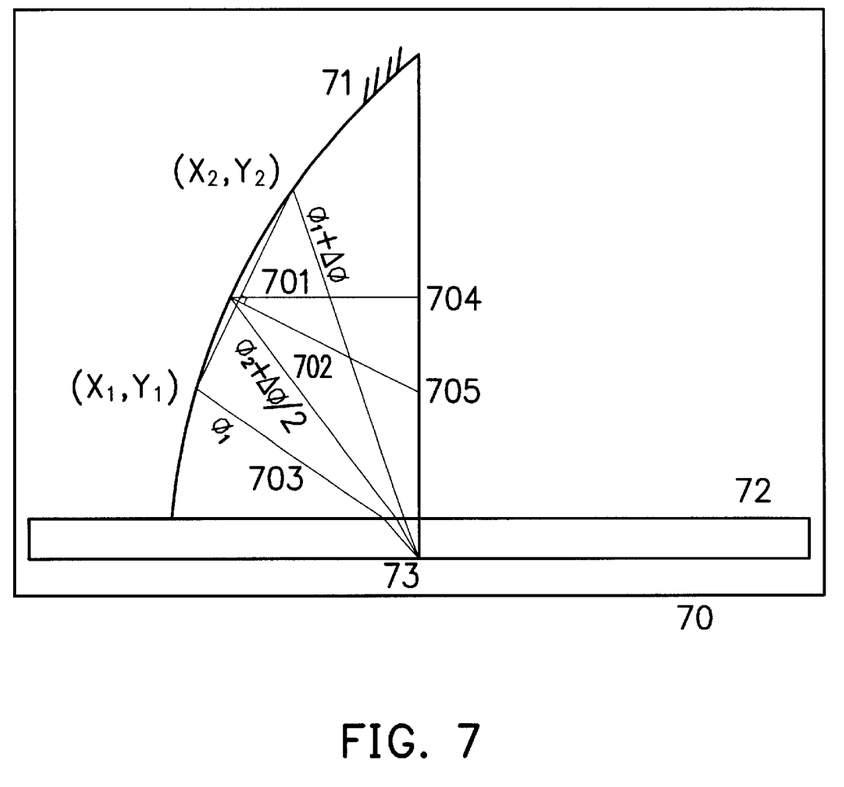
FIG. 7 is a schematic view showing how to use a numerical analysis to design a quasi-parabolic mirror.

The quasi-parabolic mirror is used to approach the function of a parabolic mirror and can compensate the deviation of the detected point caused by the observing dielectric. The quasi-parabolic mirror with a non-resolution curve can not be expressed by a mathematical formula and therefore, it must be obtained by a numerical analysis. FIG. 7 shows that how to use a numerical analysis to design the quasi-parabolic mirror where the aberration can be calibrated. Its derivation is briefly shown as follows: first, assume that point (x1, y1) is already known. After a detecting light beam is reflected at this point of the quasi-parabolic mirror with an incident angle $\phi 1$, extending lines corresponding to other incident angles can be easily drawn. As shown in FIG. 7, an incident direction 702 having an incident angle $(\phi 1+\Delta\phi/2)$ and an incident direction 701 having an incident angle $(\phi 1+\Delta\phi)$ are already known. Since the optical paths of these two incident directions are those of a parallel incident light beam after being reflected by the quasi-parabolic mirror 71, a curve is formed by the segments perpendicular to the parallel incident light beam 704 and the angle-bisecting, line 705 of the incident angle $(\phi 1+\Delta\phi/2)$. Then, the direction of this curve is extended towards a point (x2, y2) intersecting with the incident light beam having an incident angle $(\phi 1+\Delta\phi)$ (i.e., the next point of this curve). As to the position of a first point it can be arbitrarily decided, depending on the size of an apparatus used and the range of an incident angle.

Figure 8:
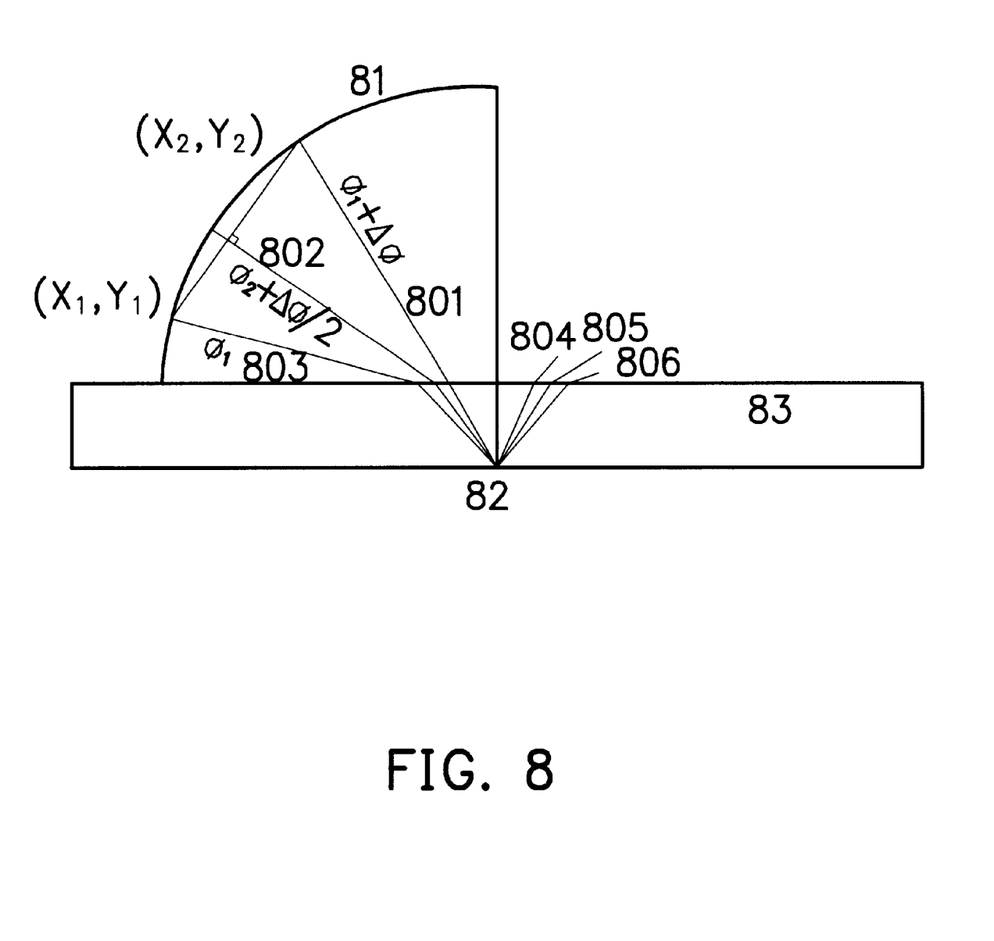
FIG. 8 is a schematic view showing how to use a numerical analysis to design the quasi-paraibolic mirror.

The quasi-concave spherical mirror which is used to approach the function of a concave spherical mirror can compensate the deviation of a detected point caused by an observing dielectric. The quasi-concave spherical mirror with a non-resolution curve can not be expressed by a mathematical formula, and therefore, it must be obtained by a numerical analysis. FIG. 8 shows that how to use a numerical analysis to design the quasi-parabolic mirror where the phase difference can be calibrated. Its derivation is briefly shown as follows: first, assume that point (x1, y1) is already known. A reflected light beam 803 is generated after a detecting light beam 806 is incident onto a quasi-concave spherical mirror 81 through an observing dielectric 82. The reflected light beam 803 is overlapped with the incident detecting light beam 806 along the original incident direction. The detecting light beam 806 has an incident angle $\phi 1$ at a detected point. Since the refractive index of an observing dielectric 82 is already known, the extending lines corresponding to other incident angles can be easily drawn. Therefore, an incident direction 82 having an incident angle $(\phi 1+\Delta\phi/2)$ and an incident direction 81 having an incident angle $(\phi 1+\Delta\phi)$ can be known. In order to remain optical paths unchanged, the optical path of a reflected incident light beam on the quasi-parabolic mirror must be overlapped with that of an incident light beam. Therefore, quasi-concave spherical curve segments extending from the point (x1, y1) is perpendicular to an incident light beam 802 to thereby determine the direction of the curve. After that, the curve is extended to a point (x2, y2) where the incident light beam 801 intersects thereto. As to the position of a first point, it can be arbitrarily decided, depending one the size of an apparatus used and the range of an incident angle.

Figure 9:
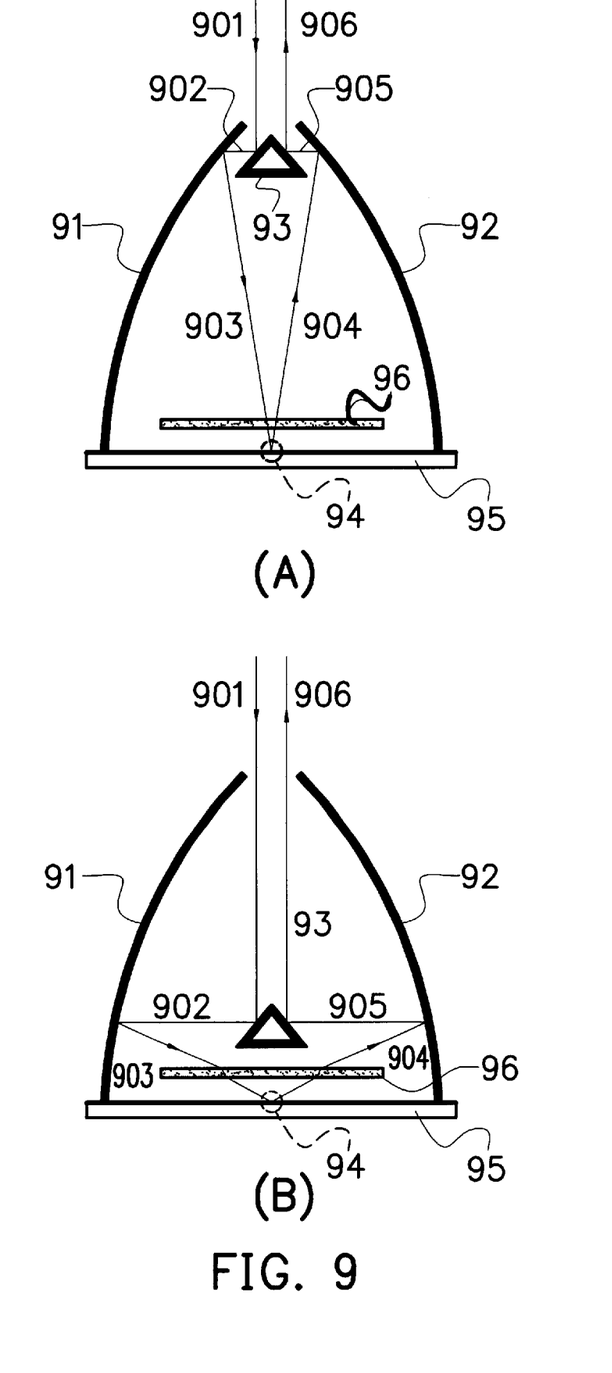
FIGS. 9(A) and 9(B) are schematic views showing a dielectric penetrating/quasi-parabolic mirror type incident angle changeable optical mechanism.

FIGS. 9(A) and 9(B) show a dielectric penetrating/quasi-parabolic mirror type incident angle changeable optical mechanism which is developed according to the principle of the above-stated quasi-parabolic mirror. Furthermore, a triangular reflecting prism 93 is used to separate the optical paths of an incident light beam and a reflected light beam from each other. As shown in FIGS. 9(A) and 9(B), the dielectric penetrating/quasi-parabolic mirror type incident angle changeable optical mechanism includes two quasi-parabolic minor 91, 92 and a triangular reflecting prism 93 which can be moved up and down using a single axis shift stage. An incident light beam 901 is reflected by the triangular reflecting prism 93 and the quasi-parabolic mirror 91 in order to thereby generate a reflected light beam 903. Due to the property of the quasi-parabolic mirror, the incident light beam 903 can penetrate an observing dielectric 96 and then incident onto a specific detecting point 94 of a sample 95. A light beam 904 reflected coming from the sample 95 is further reflected by the quasi-parabolic mirror 92 and the triangular reflecting prism 93 in order to generate a reflected light beam 906 which is parallel to the incident light beam 901. Accordingly, the relationship between the intensity and phase of the reflected light beam 906 can be obtained using an optical detector or an optical microscope to thereby derive the property of the surface of the detect-waiting sample 95.

Figure 10:
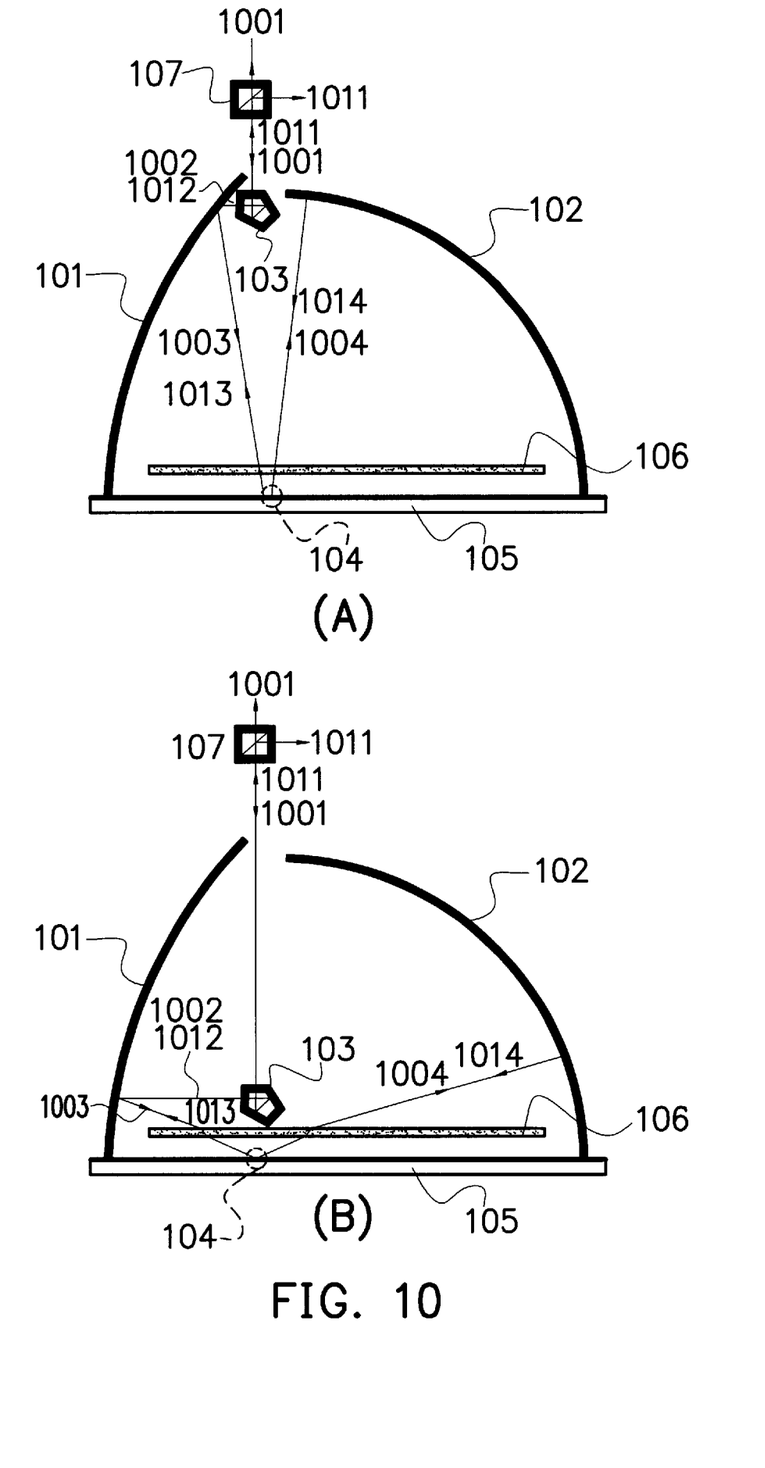
FIGS. 10(A) and 10(B) are schematic views showing a dielectric penetrating/quasi-parabolic spherical mirror type incident angle changeable optical mechanism.

FIGS. 10(A) and 10(B) show a dielectric pretreating/quasi-parabolic spherical mirror type incident angle changeable optical mechanism which is developed according to the design principle of the above-stated quasi-parabolic mirror and the quasi-concave spherical mirror. In this optical mechanism, a pentagonal reflecting prism 103 is used to overlap the optical paths of an incident light beam and an reflected light beam. As shown in FIGS 10(A) and 10(B), the dielectric penetrating/quasi-parabolic spherical mirror type incident angle changeable optical mechanism includes a quasi-parabolic mirror 101, a quasi-concave spherical mirror 102, a pentagonal reflecting prism 103 which can be moved up and down using a single axis shift stage and a non-polarized beam splitter 107. An incident light beam 1001 is reflected by the pentagonal reflecting prism 103 and the quasi-parabolic mirror 101 in order to generate a reflected light beam 1003. Due to the property of the quasi-parabolic mirror, the light beam 1003 can penetrate a dielectric 106 and then incident onto a detected point 104 of a sample 105 to generate a reflected light beam 1004. The light beam 1004 is reflected back by the quasi-concave spherical mirror 102 along an original optical paths. With such reason, a non-polarization spectroscope is additionally used to separate the overlapped incident light beam 1001 and reflected light beam 1011 with each other. The relationship of the intensity and phase of the separated reflected light beam 1011 can be obtained using an optical detector or an optical microscope thereby deriving the property of the surface of the detect-waiting sample 105. In the invention, an Ellipsometer is used as a measuring apparatus.

In summary, an optical mechanism according to the present invention can precisely control the angle of an incident light beam within a large incident angle range.

While the invention has been described by way of example and in terms of the preferred embodiment, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. An optical path overlapping type incident angle changeable optical mechanism, which allows an incident light beam to be incident onto a measured range of a sample within a large incident angle range, comprising:
    a reflecting prism reflecting the incident light beam to generate a reflected light beam having an angle of 90° with respect to the incident light beam;
    a concave parabolic cylindric mirror guiding the reflected light beam coming from the reflecting prism to a measured range of a detect-waiting sample to thereby be further reflected to generate a detect-waiting light beam;
    a concave cylindric mirror used to make the detect-waiting light beam incident onto/reflected by the reflecting prism so as to overlap with the incident light beam; and
    a light beam splitting means used to separate the detect-waiting light beam from the incident light beam.

2. The optical mechanism as claimed in claim 1, wherein the reflecting prism is a reflecting mirror.

3. The optical mechanism as claimed in claim 1, wherein the reflecting prism is a pentagonal reflecting prism.

4. The optical mechanism as claimed in claim 1, wherein the light beam splitting means is a polarizing spectroscope.

5. The optical mechanism as claimed in claim 1, wherein the light beam splitting means is a non-polarized beam splitter.

6. A dielectric penetrating/optical path overlapping type incident angle changeable optical mechanism, which allows an incident light beam to penetrate an observing dielectric having a specific thickness and then incident onto a measured range of a sample within a large incident angle range, comprising:
    a reflecting prism which reflects the incident light beam to generate a reflected light beam having an angle of 90° with respect to the incident light beam;
    a quasi-concave parabolic cylindric mirror used to make the reflected light beam coming from the reflecting prism penetrate the observing dielectric and then incident onto/reflected by a measured range of a detect-waiting sample to thereby generate a detect-waiting light beam;
    a quasi-concave cylindric mirror used to change the traveling direction of the detect-waiting light beam so as to make the detect-waiting light beam incident onto/reflected by the reflecting prism to thereby overlap with the incident light beam; and
    a light beam splitting means used to separate the detect-waiting light beam from the incident light beam.

7. The optical mechanism as claimed in claim 6, wherein the observing dielectric is a translucent dielectric.

8. The optical mechanism as claimed in claim 6, wherein the dielectric is a transparent dielectric.

9. The optical mechanism as claimed in claim 6, wherein the reflecting prism is a reflecting mirror.

10. The optical mechanism as claimed in claim 6, wherein the reflecting prism is a pentagonal reflecting prism.

11. The optical mechanism as claimed in claim 6, wherein the light beam splitting means is a polarizing spectroscope.

12. The optical mechanism as claimed in claim 6, wherein the light beam splitting means is a non-polarized beam splitter.

13. An optical path splitting type incident angle changeable optical mechanism, which allows an incident light beam to be incident onto a measured range of a sample within a large incident angle range, comprising:
    a reflecting prism which reflects the incident light beam to generate a reflected light beam having an angle of 90° with respect to the incident light beam;
    a fist concave parabolic cylindric mirror used to guide the reflected light beam coming from the reflecting prism to a measured range of a detect-waiting sample to thereby be further reflected to generate a detect-waiting light beam;
    a second concave parabolic cylindric mirror used to change the traveling direction of the detect-waiting light beam so as to make the detect-waiting light beam reflected by the reflecting prism and then parallel to the incident light beam.

14. The optical mechanism as claimed in claim 13, wherein the reflecting prism is a triangular reflecting prism.

15. A dielectric penetrating/optical path splitting type incident angle changeable optical mechanism, which allows an incident light beam to penetrate an observing dielectric having a specific thickness and then incident onto a measured range of a sample within a large incident angle range, comprising:
    a reflecting, prism which reflects the incident light beam to generate a reflected light beam having an angle of 90° with respect to the incident light beam;
    a first quasi-concave parabolic cylindric mirror used to make the reflected light beam coming from the reflecting prism penetrate the observing dielectric and then incident onto/reflected by a measured range of a detect-waiting sample to thereby generate a detect-waiting light beam;
    a second quasi-concave parabolic cylindric mirror used to change the traveling direction of the detect-waiting light beam so as to make the detect-waiting light beam reflected by the reflecting prism and then parallel to the incident light beam.

16. The optical mechanism as claimed in claim 15, wherein the observing dielectric is a translucent dielectric.

17. The optical mechanism as claimed in claim 15, wherein the observing dielectric is a transparent dielectric.

18. The optical mechanism as claimed in claim 15, wherein the reflecting prism is a triangular reflecting prism.

19. An optical path overlapping type incident angle changeable optical mechanism, which allows an incident light beam to be incident onto a measured range of a sample within a large incident angle range, comprising:

a reflecting prism reflecting the incident light beam to generate a reflected light beam having an angle of 90° with respect to the incident light beam;

a concave parabolic mirror guiding the reflected light beam coming from the reflecting prism to a measured range of a detect-waiting sample to thereby be further reflected to generate a detect-waiting light beam;

a concave spherical mirror used to make the detect-waiting light beam incident onto/reflected by the reflecting prism so as to overlap with the incident light beam; and a light beam splitting means used to separate the detect-waiting light beam from the incident light beam.

20. The optical mechanism as claimed in claim 19, wherein the reflecting prism is a reflecting mirror.

21. The optical mechanism as claimed in claim 19, wherein the reflecting prism is a pentagonal reflecting prism.

22. The optical mechanism as claimed in claim 19, wherein the light beam splitting means is a polarizing spectroscope.

23. The optical mechanism as claimed in claim 19, wherein the light beam splitting means is a non-polarized beam splitter.

24. A dielectric penetrating/optical path overlapping type incident angle changeable optical mechanism, which allows an incident light beam to penetrate an observing dielectric having a specific thickness and to then incident onto a measured range of a sample within a large incident angle range, comprising:

a reflecting prism reflecting the incident light beam to generate a reflected light beam having an angle of 90° with respect to the incident light beam;

a quasi-concave parabolic mirror used to make the reflected light beam coming from the reflecting prism penetrate the observing dielectric and then incident onto/reflected by a measured range of a detect-waiting sample to thereby generate a detect-waiting light beam;

a quasi-concave spherical mirror used to change the traveling direction of the detect-waiting light beam so as to make the detect-waiting light beam incident onto the reflecting prism to thereby overlap with the incident light beam;

a light beam splitting means used to separate the detect-waiting light beam from the incident light beam.

25. The optical mechanism as claimed in claim 24, wherein the observing dielectric is a translucent dielectric.

26. The optical mechanism as claimed in claim 24, wherein the dielectric is a transparent dielectric.

27. The optical mechanism as claimed in claim 24, wherein the reflecting prism is a reflectinig mirror.

28. The optical mechanism as claimed in claim 24, wherein the reflecting prism is a pentagonal reflecting prism.

29. The optical mechanism as claimed in claim 24, wherein the light beam splitting means is a polarizing spectroscope.

30. The optical mechanism as claimed in claim 24, wherein the light beam splitting means is a non-polarized beam splitter.

31. An optical path splitting type incident angle changeable optical mechanism, which allows an incident light beam to be incident onto a measured range of a sample within a large incident angle range, comprising:

a reflecting prism reflecting the incident light beam to generate a reflected light beam having an angle of 90° with respect to the incident light beam;

a first concave parabolic mirror used to guide the reflected light beam coming from the reflecting prism to a measured range of a detect-waiting sample to thereby be further reflected to generate a detect-waiting light beam;

a second concave parabolic mirror used to change the traveling direction of the detect-waiting light beam so as to make the detect-waiting light beam reflected by the reflecting prism and then parallel to the incident light beam.

32. The optical mechanism as claimed in claim 31, wherein the reflecting prism is a triangular reflecting prism.

33. A dielectric penetrating/optical path splitting incident angle changeable optical mechanism, which allows an incident light beam to penetrate an observing dielectric having a specific thickness and then incident onto a measured range of a sample within a large incident angle range comprising:

a reflecting prism reflecting the incident light beam to generate a reflected light beam having an angle of 90° with respect to the incident light beam;

a first quasi-concave parabolic mirror used to make the reflected light beam coming from the reflecting prism penetrate the observing dielectric and then incident onto/reflected by a measured range of a detect-waiting sample to generate a detect-waiting light beam; and a second quasi-concave parabolic mirror used to change the traveling direction of the detect-waiting light beam so as to make the detect-waiting light beam reflected by the reflecting prism and then parallel to the incident light beam.

34. The optical mechanism as claimed in claim 33, wherein the observing dielectric is a translucent dielectric.

35. The optical mechanism as claimed in claim 33, wherein the observing dielectric is a transparent dielectric.

36. The optical mechanism as claimed in claim 33, wherein the reflecting prism is a triangular reflecting prism.

* * * * *